United States Patent [19]
Moorty et al.

[11] Patent Number: 5,827,521
[45] Date of Patent: Oct. 27, 1998

[54] SHELF STABLE INSECT REPELLENT, INSECT GROWTH REGULATOR AND INSECTICIDAL FORMULATIONS PREPARED FROM TECHNICAL AZADIRACHTIN ISOLATED FROM THE KERNEL EXTRACT OF *AZADIRACHTA INDICA*

[75] Inventors: Sistla Ramchandra Moorty, Hyderabad; Annam Dilip Kumar, Secunderabad, both of India

[73] Assignee: Fortune Biotech Limited, Secunderabad, India

[21] Appl. No.: 401,242

[22] Filed: Mar. 9, 1995

[51] Int. Cl.$^6$ ........................................... A01N 25/00
[52] U.S. Cl. ..................... 424/405; 424/60; 514/453; 554/14; 554/183; 504/101; 528/1
[58] Field of Search .................. 424/405, 60; 514/453; 554/14, 183; 504/101; 528/1

[56] References Cited

U.S. PATENT DOCUMENTS

| | | | |
|---|---|---|---|
| 4,556,562 | 12/1985 | Larson | 424/195.1 |
| 4,943,434 | 7/1990 | Lidert | 424/195.1 |
| 4,946,681 | 8/1990 | Walter | 424/195.1 |
| 5,124,349 | 6/1992 | Carter et al. | 514/453 |
| 5,368,856 | 11/1994 | Locke et al. | 424/195.1 |
| 5,391,779 | 2/1995 | Lidert | 514/453 |
| 5,397,571 | 3/1995 | Roland et al. | 424/405 |

OTHER PUBLICATIONS

Yamasaki et al., "Isolation and Purification of Azadirachtin from Neem (*Azadirachta Indica*) Seeds Using Flash Chromatography and High–Performance Liquid Chromatography", *J. of Chromatography,* 356 (1986) 220–226.

*Primary Examiner*—Samuel A. Acquah
*Attorney, Agent, or Firm*—Sughrue, Mion, Zinn, Macpeak & Seas

[57] ABSTRACT

Storage stable azadirachtin, an insect repellent and insect growth regulator, and insecticidal formulations (emulsifiable concentrate) thereof, are prepared from purified neem kernel extract, with an active ingredient content of 0.3% to 4% and characterized by the absence of gums and aflatoxin spores, for example. The aforementioned formulations contain solvents belonging to the class of aliphatic dihydroxylated alcohols of more than 80% by volume and optionally containing sunscreens and antioxidants.

50 Claims, No Drawings

SHELF STABLE INSECT REPELLENT, INSECT GROWTH REGULATOR AND INSECTICIDAL FORMULATIONS PREPARED FROM TECHNICAL AZADIRACHTIN ISOLATED FROM THE KERNEL EXTRACT OF *AZADIRACHTA INDICA*

The invention relates to shelf life stable, insect repellent, insect growth regulator and insecticidal formulations having an azadirachtin content ranging between 0.3 to 4%, technical azadirachtin composition of high purity and methods for preparing same.

BACKGROUND OF THE INVENTION

The insect repellent, insect growth regulator and insecticidal azadirachtin, and associated molecules thereof, isolated from the kernels of *Azadirachta indica* are well documented. "Neem, A Tree For Solving Global Problems" (1992) National Research Council, National Academy Press, Washington D.C.

Various methods for extracting azadirachtin from neem kernels using protic as well as aprotic solvents are published. Those processes generally relate to the use of one solvent, concentration to remove the solvent and water and finally formulating the azadirachtin to the desired percentage, depending on the purity and concentration of azadirachtin.

It now has been uncovered that the most significant drawback in the aforementioned processes is retention of gums which retain water present in the kernel, thus destabilising formulations.

SUMMARY OF THE INVENTION

It is an object of the instant invention to provide an improved composition and process for extracting stable, technical azadirachtin free of spores and fungal toxins, excess gums and water, suitable for formulations containing 0.3–4%, or higher, of active ingredient. The impurities removed by the claimed process have a destabilising effect on the active ingredient.

Another object of the instant invention is to provide a process for preparing shelf stable azadirachtin formulations which are easily dispersible in water, have a high concentration of active ingredient and are stable on storage as well as when applied to plants comprising glycols or diols as solvent.

DETAILED DESCRIPTION OF INVENTION

In accordance with the instant invention there is provided a simple but innovative process for extracting azadirachtin without using solvent mixtures or chromatographic techniques using, in part, glycols or diols, with more than two carbon atoms, as solvent.

Since stability of a formulation depends on removal of impurities (which destabilize the formulation) from technical azadirachtin, a process has been developed for removal of gums which retain water and have a destabilising influence on the technical as well as formulated product.

Available formulations claim a retention of 80% of active ingredient activity during a fixed shelf life period whereas a formulated product herein retains more than 90% of active ingredient activity over that same time period.

Azadirachtin formulations in the novel glycol or diol solvent have better dispersibility. When suspended in water, the formulation provides for longer retention at the leaf surface thus providing enhanced efficacy. Moreover, the instant formulations are devoid of phytotoxicity encountered with other formulations.

The instant invention provides for a multistep method for purifying azadirachtin from neem seeds and compositions of extended shelf life.

The phrase, "extended shelf life" is meant to indicate that on storage at ambient conditions, generally in an air-tight container at 25° C., a composition of the instant invention retains 90% or more azadirachtin activity after at least a 12-month storage period.

The seeds of the neem tree (*Azadirachta indica* A. Juss) are the starting material. The neem seeds can be dried and stored at temperatures not below 10° C. and not exceeding 35° C. The seeds can be stored for up to a year before processing.

The seeds, fresh or dried, are pulverized to a size of about 0.25 mm in diameter in preparation of the extraction procedure. The pulverizing step should not take place more than 1 day before extraction is to ensue. The size of the particles is not overly critical, from 0.25 mm in diameter to about 0.5 mm in diameter is suitable.

The pulverized neem fruit is soaked in a hydroxylic solvent, such as an aliphatic monohydroxylated alcohol. The aliphatic monohydroxylate alcohol has a size from 1 to about 8 carbon atoms and preferably from 1 to about 4 carbon atoms. Suitable alcohols include methanol, ethanol, isopropanol and butanol, with methanol preferred.

At least a 1:2 ratio, by weight, of neem to aliphatic monohydroxylated alcohol is used. The mixture is agitated continuously over a period of at least ten hours at a temperature at least at room temperature and not exceeding 50° C. The mixture then is separated by known means, such as centrifugation, filtration or mere decanting.

The liquid phase is collected and concentrated, for example, by evaporation or, more quickly under vacuum, to provide a neem extract concentrate. The separation and concentration steps of the neem extract should be conducted at a temperature of at least room temperature and not exceeding 45° C.

It is preferred that at least 95% of the aliphatic monohydroxylated alcohol be removed.

The resulting concentrate then is mixed with continuous stirring for at least two hours at a temperature of 30°–35° C. with a halogenated aliphatic hydrocarbon solvent at a ratio of at least 1:2–1:3, on a weight basis. Suitable halogenated aliphatic hydrocarbons are chlorinated. Examples include dichloromethane, dichloroethane, chloroform, trichloroethylene and dichloropropane. Dichloromethane is a preferred solvent.

The lower layer containing insoluble material, including gums and resins and other impurities soluble in known solvents, such as ethyl acetate, is removed, for example, by filtration using known materials and methods.

The extract is washed with water. An equal volume of water is added to the halogenated aliphatic hydrocarbon solution and slowly stirred for about fifteen minutes. Then the mixture is allowed to sit, without stirring for about 30 minutes. The lower organic phase is removed. The process can be repeated and preferably at least once more. The washing step is conducted at a temperature between 25°–35° C.

The organic layer is recovered and distilled. A preferred method is to distill the solvent under atmospheric pressure until about 90% of the solvent is removed. The balance of the solvent can be removed under reduced pressure at a temperature between 20°–40° C.

The syrupy residue is mixed with at least eight and not more than twelve volumes of aliphatic hydrocarbon solvent, such as hexane, octane or isooctane. Hexane is preferred. The residue is added slowly to stirred aliphatic hydrocarbon, at 25°–30° C. over a period of about 2–2.5 hours. The mixture is stirred for at least another thirty hours. Technical azadirachtin remains insoluble and is removed, for example, by decanting or passage of the solution through a Nutsch filter.

The liquid phase contains other recoverable products, such as neem oil and salanin.

The solid product is dried, generally in a vacuum drier at a temperature no higher than about 40°–45° C. and a pressure of about 600 mm Hg to yield the technical azadirachtin product of 10–25% purity with less than 0.5% retained moisture.

The technical azadirachtin obtained by the above-described process then can be dissolved in a aliphatic dihydroxylated alcohol solvent comprising at least 80%, by volume, and preferably 90% or more of the final preparation, at the desired concentration. Suitable aliphatic dihydroxylated alcohols include propylene glycol and other dihydroxylated alcohols of greater than two carbon atoms.

Thus, a 0.3% active ingredient composition can be obtained by adding 30 grams of technical azadirachtin of 10% purity to a suitable amount of propylene glycol to yield a final volume of one liter.

The dihydroxylated alcohol formulation can contain other non-critical excipients, such as, emulsifiers, surfactants, sunscreens, antioxidants and the like. Suitable additives include detergents and p-aminobenzoic acid. The amounts of such additives can vary according to the desired characteristics of the final preparation, cost and the like. Thus a suitable concentration of emulsifier is from 3–8%, of surfactant is from 0.5–4% and of sunscreens or antioxidants is from 0.1–1%. A sample formulation contains 5% emulsifier, 2% surfactant and 0.5% sunscreen/antioxidant.

The above technical azadirachtin can be purified further by dissolving the dried product in about 2–3 times the volume of aliphatic monohydroxylated alcohol, such as methanol as described hereinabove, at a temperature from room temperature to about 30°–35° C. Then four times the volume of added alcohol of water is added and mixed to form a slurry. The slurry is incubated for about two hours with stirring. The liquid phase is obtained, such as by filtration, and concentrated, as described hereinabove.

Then a halogenated aliphatic hydrocarbon, such as dichloromethane, essentially as described hereinabove, is added to extract the aqueous layer and the organic layer is removed. The organic layer is washed with water, as discussed hereinabove, and the remaining steps as described hereinabove following mixing with the halogenated hydrocarbon are practiced to derive a dried product of higher purity, generally of about 40% purity.

The invention now will be described by way of the following non-limiting examples.

EXAMPLES

Example 1

Eighteen tons of neem fruit are depulped, destoned, dried (9 tons) and stored in silos at temperatures not exceeding 35° C. The seeds are decorticated and pulverised a day in advance for processing. The pulverised kernels (3 tons) of 0.25 mm thickness are soaked in methanol (12 tons) for 10 hrs and passed through a decanter to separate the solid & liquid phases. The methanolic extract is concentrated under vacuum initially in a falling film evaporator and finally in an agitated thin film evaporator to recover 95% methanol.

The concentrate is treated with dichloromethane (1200 kgs) and the gums and resins which remain undissolved are removed. The extract is washed with water to remove methanol and is desolventised in an agitated thin film evaporator and the concentrate finally treated with hexane to eliminate traces of oil. The product is dried in a rotary cone vacuum drier at temp not exceeding 50° C. to give a product (60 kgs) of purify 20–25%.

The product thus obtained is devoid of oil waxes, gums, protein and water which have phytotoxicity and have a destabilising influence in storage of formulations as well as technical product.

Example 2

In general, azadirachtin insecticidal formulations of the instant invention contain more than 90% glycol or diol solvent with or without sunscreens and antioxidants. No emulsifier is added since natural emulsifier from seeds is adequate.

The formulation is prepared by dissolving 75 grams of azadirachtin technical (40–42% purity) made up to 1 litre with propylene glycol and p-amino benzoic acid (10 gms), stirring for 30 min and filtering to eliminate particulate matter before filling.

All references cited herein are incorporated by reference in entirety.

It will be evident to the artisan that various modifications and variations can be made to the invention as disclosed without departing from the spirit and scope of the instant invention.

What is claimed is:

1. A solid gum-free azadirachtin-containing composition in kilogram amounts comprising about 10% to about 25% by weight of azadirachtin.

2. A solid gum-free azadirachtin-containing composition in kilogram amounts comprising about 40% by weight of azadirachtin.

3. The solid composition of claim 1 obtained by a method comprising the steps of:

(a) grinding neem seeds to form particles;

(b) soaking said particles in an aliphatic monohydroxylated alcohol;

(c) discarding said particles and reducing the volume of said aliphatic monohydroxylated alcohol by evaporation;

(d) mixing a liquid halogenated aliphatic hydrocarbon with said reduced volume of alcohol to form a mixture of two layers;

(e) separating said halogenated hydrocarbon layer and lower layer containing insoluble material and dessicating said halogenated hydrocarbon layer to obtain a residue;

(f) suspending said residue in a liquid aliphatic hydrocarbon;

(g) removing azadirachtin-containing precipitates therefrom;

(h) dissolving said precipitates of step (g) in an aliphatic monohydroxylated alcohol;

(i) adding water thereto, mixing and recovering organic material;

(j) adding a liquid halogenated aliphatic hydrocarbon to the organic material of step (i) and mixing;

(k) repeating steps (e)–(g); and (l) drying the precipitates to obtain the azadirachtin-containing composition.

4. The solid composition of claim 3, wherein said aliphatic monohydroxylated alcohol of step (b) comprises no more than 4 carbon atoms.

5. The solid composition of claim 4, wherein said aliphatic monohydroxylated alcohol is ethanol, methanol, propanol or butanol.

6. The solid composition of claim 5, wherein said aliphatic monohydroxylated alcohol is methanol.

7. The solid composition of claim 3, wherein said step (a) is carried out at a temperature not exceeding 35° C.

8. The solid composition of claim 3, wherein said particles of step (a) are about 0.25 mm in diameter.

9. The solid composition of claim 3, wherein in said step (b), the particles are soaked for at least 10 hours.

10. The solid composition of claim 3, wherein said liquid halogenated aliphatic hydrocarbon of step (d) is chlorinated.

11. The solid composition of claim 3, wherein said liquid halogenated aliphatic hydrocarbon of step (d) has no more than three carbon atoms.

12. The solid composition of claim 11, wherein said liquid halogenated aliphatic hydrocarbon is dichloromethane, dichloroethane or dichloropropane.

13. The solid composition of claim 12, wherein said liquid halogenated aliphatic hydrocarbon is dichloromethane.

14. The solid composition of claim 3, wherein in step (e), following separating said halogenated hydrocarbon layer, said halogenated hydrocarbon is mixed with water to form a mixture of two layers and said halogenated hydrocarbon layer is removed.

15. The solid composition of claim 3, wherein said aliphatic hydrocarbon is saturated.

16. The solid composition of claim 3, wherein said aliphatic hydrocarbon has no more than ten carbon atoms.

17. The solid composition of claim 16, wherein said aliphatic hydrocarbon is hexane, octane or isooctane.

18. The solid composition of claim 17, wherein said aliphatic hydrocarbon is hexane.

19. The solid composition of claim 3, further comprising the step of filtering said mixture following step (d) and before step (e).

20. The solid composition of claim 3, wherein the volume of said aliphatic monohydroxylated alcohol in step (h) is twice the volume of precipitates.

21. The solid composition of claim 20, wherein the amount of water in step (i) is four times the volume of alcohol of step (h).

22. The solid composition of claim 2, obtained by a method comprising the steps of:

(a) grinding neem seeds to form particles;

(b) soaking said particles in an aliphatic monohydroxylated alcohol;

(c) discarding said particles and reducing the volume of said aliphatic monohydroxylated alcohol by evaporation;

(d) mixing a liquid halogenated aliphatic hydrocarbon with said reduced volume of alcohol to form a mixture of two layers;

(e) separating said halogenated aliphatic hydrocarbon layer and lower layer containing insoluble material and dessicating said hydrocarbon layer to obtain a residue;

(f) suspending said residue in a liquid aliphatic hydrocarbon;

(g) removing azadirachtin-containing precipitates therefrom; and (h) drying the precipitates to obtain the azadirachtin-containing composition.

23. The solid composition of claim 22, further comprising the step of filtering said mixture following step (d) and before step (e).

24. A method for purifying a gum-free azadirachtin-containing composition without the need for a chromatography step comprising the steps of:

(a) grinding neem seeds to form particles;

(b) soaking said particles in an aliphatic monohydroxylated alcohol;

(c) discarding said particles and reducing the volume of said aliphatic monohydroxylated alcohol by evaporation;

(d) mixing a liquid halogenated aliphatic hydrocarbon with said reduced volume of alcohol to form a mixture of two layers;

(e) separating said halogenated aliphatic hydrocarbon layer and lower layer containing insoluble material and desiccating to obtain a residue;

(f) suspending said residue in a liquid aliphatic hydrocarbon;

(g) removing azadirachtin-containing precipitates therefrom;

(h) dissolving said precipitates of step (g) in an aliphatic monohydroxylated alcohol;

(i) adding water thereto, mixing and recovering organic material;

(j) adding a liquid halogenated aliphatic hydrocarbon to the organic material of step (i) and mixing;

(k) repeating steps (e)–(g); and (l) drying to obtain the azadirachtin-containing composition.

25. The method of claim 24, wherein said aliphatic monohydroxylated alcohol of step (b) comprises no more than 4 carbon atoms.

26. The method of claim 25, wherein said aliphatic monohydroxylated alcohol is ethanol, methanol, propanol or butanol.

27. The method of claim 26, wherein said aliphatic monohydroxylated alcohol is methanol.

28. The method of claim 24, wherein said step (a) is carried out at a temperature not exceeding 35° C.

29. The method of claim 24, wherein said particles of step (a) are about 0.25 mm in diameter.

30. The method of claim 24, wherein in said step (b), the particles are soaked for at least 10 hours.

31. The method of claim 24, wherein said liquid aliphatic halogenated hydrocarbon is chlorinated.

32. The method of claim 24, wherein said liquid halogenated aliphatic hydrocarbons has no more than three carbon atoms.

33. The method of claim 32, wherein said liquid halogenated aliphatic hydrocarbon is dichloromethane, dichloroethane or dichloropropane.

34. The method of claim 33, wherein said liquid halogenated aliphatic hydrocarbon is dichloromethane.

35. The method of claim 24, wherein in step (e), following separating said halogenated hydrocarbon layer, said halogenated hydrocarbon is mixed with water to form a mixture of two layers and said halogenated hydrocarbon layer is removed.

36. The method of claim 24, wherein said aliphatic hydrocarbon is saturated.

37. The method of claim 24, wherein said aliphatic hydrocarbon has no more than ten carbon atoms.

38. The method of claim 37, wherein said aliphatic hydrocarbon is hexane, octane or isooctane.

39. The method of claim 38, wherein said aliphatic hydrocarbon is hexane.

40. The method of claim 24, wherein the volume of said aliphatic monohydroxylated alcohol in step (h) is twice the volume of precipitates.

41. The method of claim 40, wherein the amount of water in step (i) is four times the volume of alcohol of step (h).

42. The method of claim 24, further comprising the step of filtering said mixture following step (d) and before step (e).

43. A method for purifying a gum-free azadirachtin-containing composition without the need for a chromatographic step comprising the steps of:

(a) grinding neem seeds to form particles;

(b) soaking said particles in an aliphatic monohydroxylated alcohol;

(c) discarding said particles and reducing the volume of said aliphatic monohydroxylated alcohol by evaporation;

(d) mixing a liquid halogenated aliphatic hydrocarbon with said reduced volume of alcohol to form a mixture of two layers;

(e) separating said halogenated aliphatic hydrocarbon layer and lower layer containing insoluble material and desiccating to obtain a residue;

(f) suspending said residue in a liquid aliphatic hydrocarbon;

(g) removing azadirachtin-containing precipitates therefrom; and (h) drying to obtain the azadirachtin-containing composition.

44. The method of claim 43, further comprising the step of filtering said mixture following step (d) and before step (e).

45. A liquid gum-free azadirachtin-containing composition comprising about 0.3% to about 4% by weight of azadirachtin and at least 80% by volume of an aliphatic dihydroxylated alcohol containing more than two carbons.

46. The liquid composition of claim 45, further comprising an antioxidant, a sunscreen or both.

47. The liquid composition of claim 45, wherein the amount of azadirachtin by weight is about 1.5%.

48. The liquid composition of claim 45, wherein the volume of aliphatic dihydroxylated alcohol is at least 90%.

49. The liquid composition of claim 46 comprising about 1% p-aminobenzoic acid.

50. The liquid composition of claim 45, wherein said aliphatic dihydric alcohol is propylene glycol.

* * * * *